United States Patent
Cho et al.

(10) Patent No.: US 12,232,862 B2
(45) Date of Patent: Feb. 25, 2025

(54) NONINVASIVE/NON-CONTACT DEVICE AND METHOD FOR DETECTING AND DIAGNOSING SLEEP APNEA BY USING IR-UWB RADAR

(71) Applicant: IUCF-HYU (INDUSTRY-UNIVERSITY COOPERATION FOUNDATION HANYANG UNIVERSITY), Seoul (KR)

(72) Inventors: Sung Ho Cho, Seoul (KR); Seok Hyun Cho, Seoul (KR); Sun Kang, Seoul (KR)

(73) Assignee: IUCF-HYU (INDUSTRY-UNIVERSITY COOPERATION FOUNDATION HANYANG UNIVERSITY), Seoul (KR)

(*) Notice: Subject to any disclaimer, the term of this patent is extended or adjusted under 35 U.S.C. 154(b) by 727 days.

(21) Appl. No.: 17/595,876

(22) PCT Filed: May 15, 2020

(86) PCT No.: PCT/KR2020/006421
§ 371 (c)(1),
(2) Date: Nov. 29, 2021

(87) PCT Pub. No.: WO2020/242101
PCT Pub. Date: Dec. 3, 2020

(65) Prior Publication Data
US 2022/0313113 A1    Oct. 6, 2022

(30) Foreign Application Priority Data
May 30, 2019  (KR) .................. 10-2019-0063563

(51) Int. Cl.
*A61B 5/08* (2006.01)
*A61B 5/00* (2006.01)
*A61B 5/05* (2021.01)

(52) U.S. Cl.
CPC .............. *A61B 5/0826* (2013.01); *A61B 5/05* (2013.01); *A61B 5/4818* (2013.01); *A61B 5/7203* (2013.01); *A61B 5/7275* (2013.01)

(58) Field of Classification Search
CPC ............... A61B 5/0816; A61B 5/0826; A61B 5/4818; A61B 5/4815; A61B 5/4812; A61B 5/4806
See application file for complete search history.

(56) References Cited

U.S. PATENT DOCUMENTS 6,142,950 A * 11/2000 Allen .................... A61B 5/087
                                                          600/529
2011/0060215 A1 * 3/2011 Tupin, Jr. ............. A61B 5/1075
                                                          600/407
2018/0049669 A1    2/2018 Vu et al.

FOREIGN PATENT DOCUMENTS

JP    10-2016-0148904 A    12/2016
JP    10-2018-0049761 A    5/2018
(Continued)

OTHER PUBLICATIONS

International Search Report for PCT/KR2020/006421, dated Aug. 21, 2020.

*Primary Examiner* — Gerald Johnson
(74) *Attorney, Agent, or Firm* — Sughrue Mion, PLLC

(57) ABSTRACT

The present invention may provide a device and a method for detecting and diagnosing sleep apnea, which can accurately determine an apnea state by: extracting a respiration signal of an examinee from a received signal which is a reflection of an impulse signal emitted from at least one IR-UWB radar; setting a threshold value for determining an (Continued)

apnea state from changes in the deviation and interval between peaks of the extracted respiration signal; and comparing the set threshold value with the deviation between the peaks. Therefore, the sleep apnea can be accurately detected and diagnosed using a non-contact/noninvasive method, and thus inconvenience felt by the examinee can be reduced.

8 Claims, 6 Drawing Sheets

(56) References Cited

FOREIGN PATENT DOCUMENTS

| | | |
|---|---|---|
| KR | 10-2014-0003867 A | 1/2014 |
| KR | 10-2014-0006256 A | 1/2014 |
| KR | 10-1836761 B1 | 3/2018 |
| KR | 10-2018-0109100 A | 10/2018 |
| WO | 2014/159773 A1 | 10/2014 |

* cited by examiner

NONINVASIVE/NON-CONTACT DEVICE AND METHOD FOR DETECTING AND DIAGNOSING SLEEP APNEA BY USING IR-UWB RADAR

CROSS REFERENCE TO RELATED APPLICATIONS

This application is a National Stage of International Application No. PCT/KR2020/006421 filed May 15, 2020, claiming priority based on Korean Patent Application No. 10-2019-0063563 filed May 30, 2019.

Technical Field

The present invention relates to a device and a method for detecting and diagnosing sleep apnea, and more particularly, to a device and a method for detecting and diagnosing sleep apnea in a non-contact/non-invasive manner using an impulse radio ultra-wideband (IR-UWB) radar.

Background Art

Currently, polysomnography is mainly used as a sleep monitoring method. Polysomnography is a test method that systematically and accurately analyzes various events that occur during sleep using a plurality of contact type sensors attached to an examinee. In general, polysomnography is performed in such a manner that sensors are attached to a nose, an abdomen, a chest, and the like, at which vital signs related to respiration of an examinee may be obtained, and an examiner monitors events occurring in an examinee through the attached sensors.

However, since polysomnography uses contact type sensors, a test should be performed in a state in which an examinee sleeps while wearing the sensors. Therefore, there is a problem in that it is difficult for the examinee to get comfortable sleep because movement of the examinee is restricted during the test. In addition, there is an inconvenience in that an examiner should continuously perform monitoring during a test period in order to continuously check whether the sensors are stably attached to the examinee.

Various sensors have been researched and developed to solve such problems of polysomnography, but since the sensors do not provide a level of accuracy required in the field, there is still a continuing need for a device and method capable of accurately detecting and diagnosing sleep apnea of an examinee in a non-contact/non-invasive method.

Disclosure

Technical Problem

The present invention is directed to providing a device and a method for detecting and diagnosing sleep apnea, which are capable of accurately diagnosing sleep apnea in a non-contact/non-invasive manner.

The present invention is also directed to providing a device and a method for detecting and diagnosing sleep apnea, which enable automatic monitoring without requiring continuous monitoring of an examiner.

The present invention is also directed to providing a device and a method for detecting and diagnosing sleep apnea, which are capable of detecting and diagnosing sleep apnea by analyzing a respiration signal of an examinee acquired using an impulse radio ultra-wideband (IR-UWB) radar in a time domain without conversion to a frequency domain.

Technical Solution

According to one embodiment of the present invention, a device for detecting and diagnosing sleep apnea includes a signal acquisition unit configured to acquire clutter subtraction signals by removing a clutter signal from reception signals received when impulse signals are emitted from one or more impulse radio ultra-wideband (IR-UWB) radars disposed at predetermined positions and are reflected, a respiration signal extraction unit configured to determine a position at which a change is greatest in the plurality of clutter subtraction signals acquired during a predetermined signal acquisition period, extract the clutter subtraction signal at the determined position to acquire a respiration signal that is a respiration waveform signal, and detect a local maximum value and a local minimum value that are peaks of the respiration signal, a threshold value setting unit configured to accumulate deviations between the local maximum value and the local minimum value to set a first threshold value that is a criterion for a normal state, set a first weight for determining a start of an apnea state according to a change in the local maximum value or the local minimum value, set a second weight for determining an end of the apnea state according to a change in the number of the local maximum values and the local minimum values obtained during a predetermined reference time period, and set a second threshold value, which is a criterion for determining the apnea state, from the first threshold value and the first and second weights, and a detection diagnosis unit configured to compare the deviation with the second threshold value to detect the apnea state and diagnose a level of sleep apnea of an examinee based on the number of times of the detected apnea state.

The threshold value setting unit may include a first threshold value setting unit configured to accumulate the deviations between the local maximum value and the local minimum value and set a deviation corresponding to a predetermined lower proportion among the accumulated deviations as the first threshold value, a weight setting unit configured to compare a ratio of a previous local maximum value to a current local maximum value or a ratio of a previous local minimum value to the local minimum value with a predetermined first reference ratio at a reference time point, set the first weight to different predetermined values according to a comparison result, and set the second weight to different predetermined values according to a ratio of the number of the local maximum values and the local minimum values obtained during the reference time period before the reference time point to the number of the local maximum values and the local minimum values obtained during the reference time period after the reference time point, and a second threshold value setting unit configured to set the second threshold value by multiplying the first threshold value changed over time by the first and second weights.

The weight setting unit may apply the first weight during a predetermined first weight period from the reference time point and apply the second weight during a predetermined second weight period before the reference time point.

The weight setting unit may include an apnea detection unit configured to compare the deviation with the second threshold value in a unit of a predetermined detection period and, when the deviation is greater than or equal to the second threshold value, detect the apnea state, and an apnea diagnosis unit configured to determine the level of sleep apnea of the examinee according to the number of times of the detected apnea state per total sleep time.

According to another embodiment of the present invention, a method of detecting and diagnosing sleep apnea includes removing a clutter signal from reception signals, which are received when impulse signals are emitted from one or more IR-UWB radars disposed at predetermined positions and are reflected, to acquire clutter subtraction signals, determining a position at which a change is greatest in the plurality of clutter subtraction signals acquired during a predetermined signal acquisition period, extracting the clutter subtraction signal at the determined position to acquire a respiration signal that is a respiration waveform signal, and detecting a local maximum value and a local minimum value that are peaks of the respiration signal, accumulating deviations between the local maximum value and the local minimum value to set a first threshold value that is a criterion for a normal state, setting a first weight for determining a start of an apnea state according to a change in the local maximum value or the local minimum value, setting a second weight for determining an end of the apnea state according to a change in the number of the local maximum values and the local minimum values obtained during a predetermined reference time period, and setting a second threshold value, which is a criterion for determining the apnea state, from the first threshold value and the first and second weights, and comparing the deviation with the second threshold value to detect the apnea state and diagnosing a level of sleep apnea of an examinee based on the number of times of the detected apnea state.

Advantageous Effects

Therefore, a device and a method for detecting and diagnosing sleep apnea according to embodiments of the present invention can accurately detect and diagnose sleep apnea in a non-contact/non-invasive manner using an impulse radio ultra-wideband (IR-UWB) radar, thereby reducing the inconvenience of an examinee. Since automatic monitoring is possible using previously developed occupancy detection and biosignal extraction technologies, continuous monitoring of an examiner is not required, thereby detecting and diagnosing sleep apnea regardless of time and place. In addition, sleep apnea can be detected and diagnosed without converting a signal in a time domain acquired using an IR-UWB radar being into a frequency domain, thereby manufacturing a device at low costs.

Modes of the Invention

Figure 1:
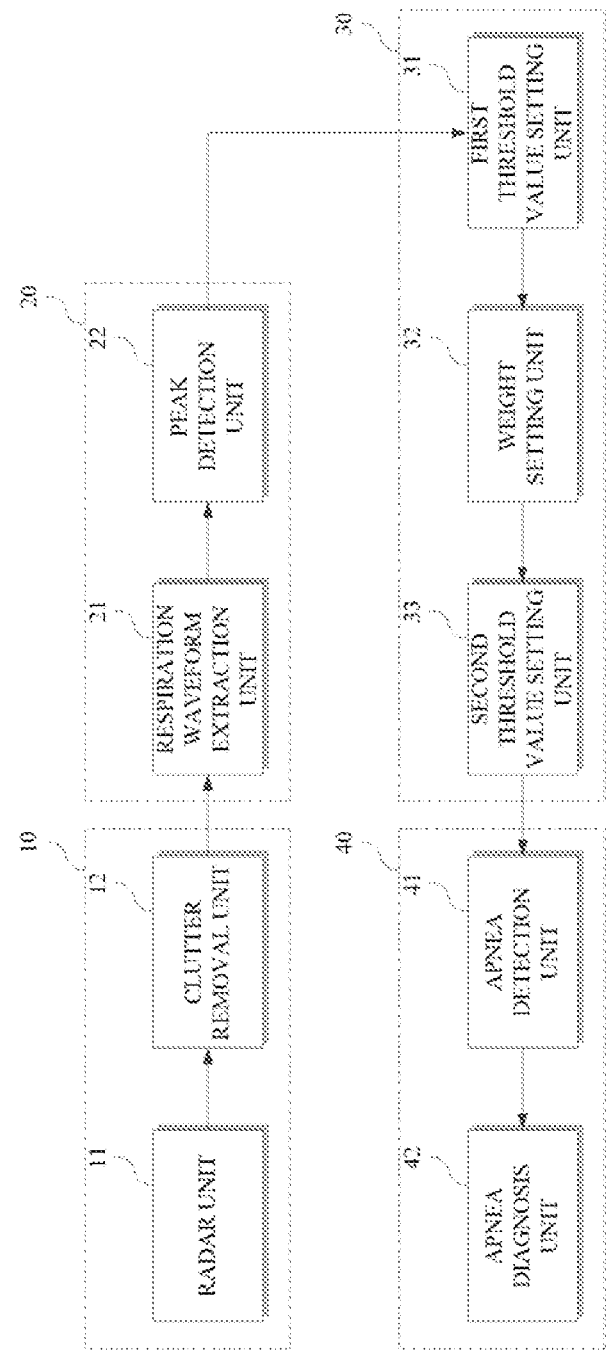
FIG. 1 illustrates a schematic structure of a device for detecting and diagnosing sleep apnea according to one embodiment of the present invention.

In order to fully understand the present invention, operational advantages of the present invention, and objects achieved by the implementation of the present invention, the accompanying drawings illustrating exemplary embodiments of the present invention and the contents described in the accompanying drawings need to be referred to.

Hereinafter, the present invention will be described in detail by describing exemplary embodiments of the present invention with reference to the accompanying drawing. However, the present invention may be implemented in various forms and is not limited to the embodiments described herein. In order to clearly describe the present invention, portions that are not associated with a description will be omitted, and like reference numerals denote like members. Throughout the present specification, unless explicitly described to the contrary, "comprising" any components will be understood to imply the inclusion of other elements rather than the exclusion of any other elements. In addition, a term "~unit", "~er/or," "module," "block," or the like described in the specification means a processing unit of at least one function or operation and may be implemented by hardware or software or a combination of hardware and software.

Figure 2:
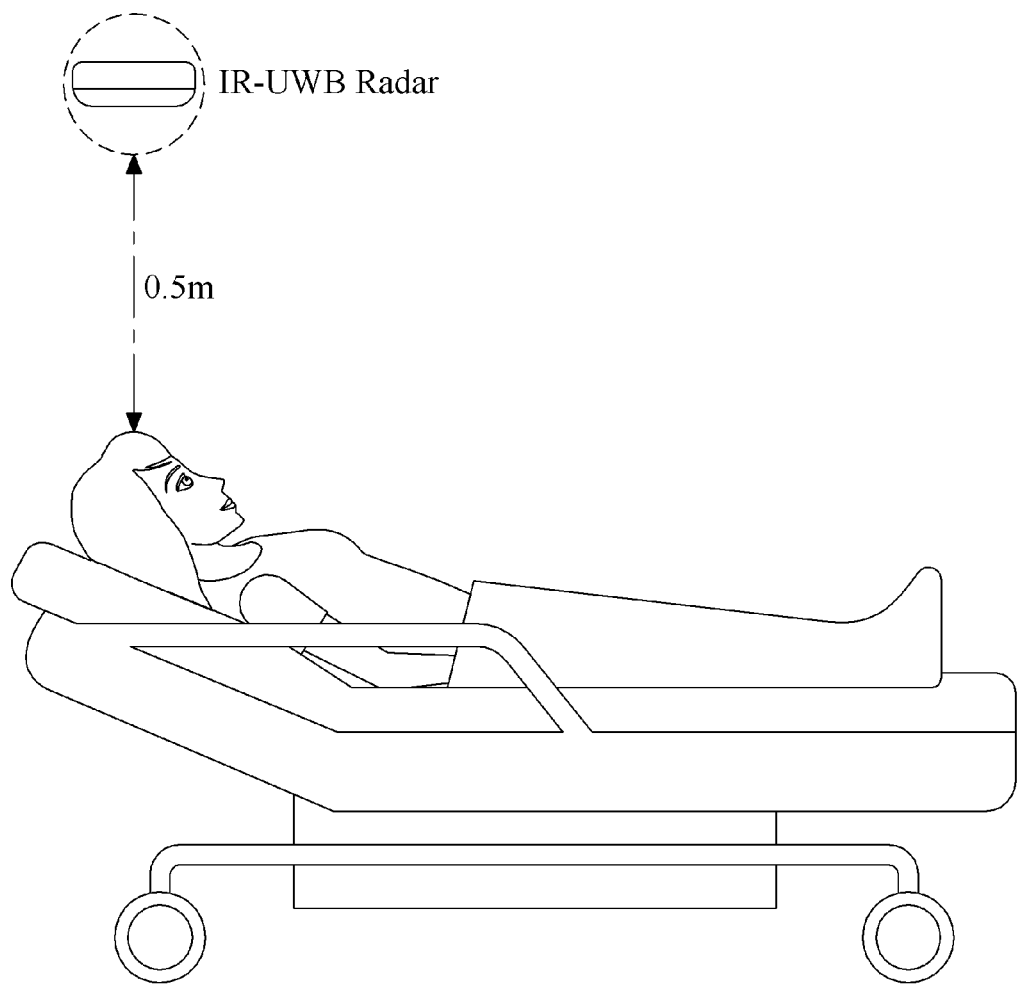
FIG. 2 illustrates an example of an environment for detecting and diagnosing sleep apnea according to the present embodiment.
Figure 3:
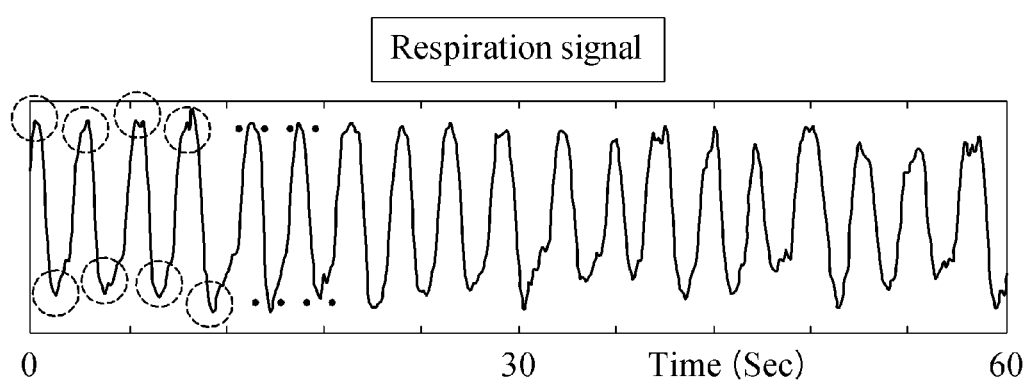
FIG. 3 illustrates an example of a respiration signal acquired by a respiration waveform extraction unit of FIG. 1.
Figure 4A:
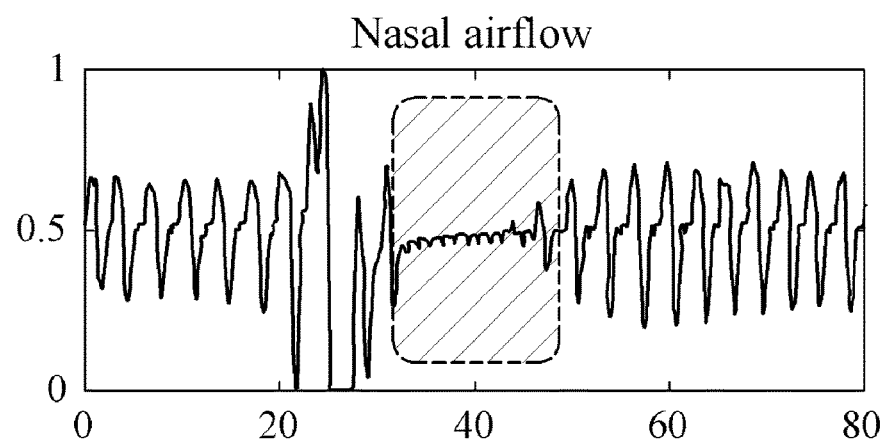
FIGS. 4A-4C illustrate respiratory activities detected at a nose and an abdomen and respiratory signals detected using a radar during central sleep apnea.
Figure 4B:
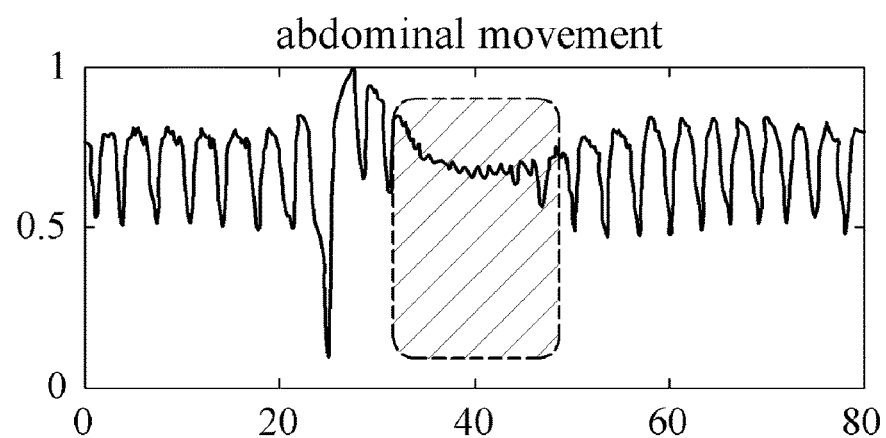
Figure 4C:
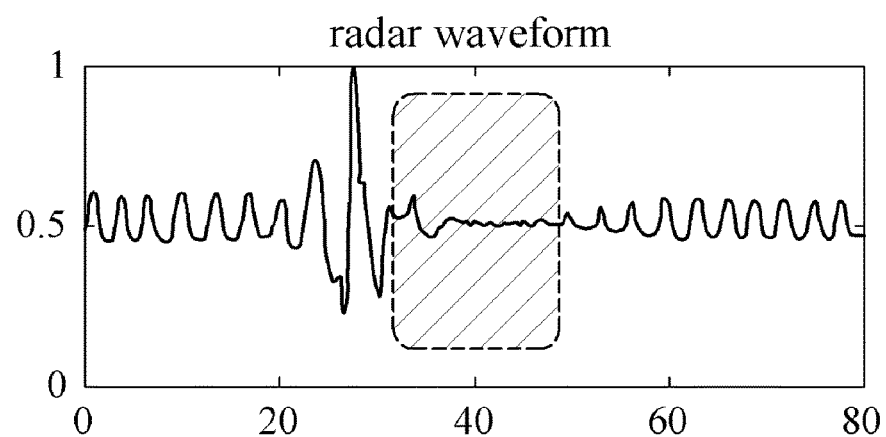
Figure 5:
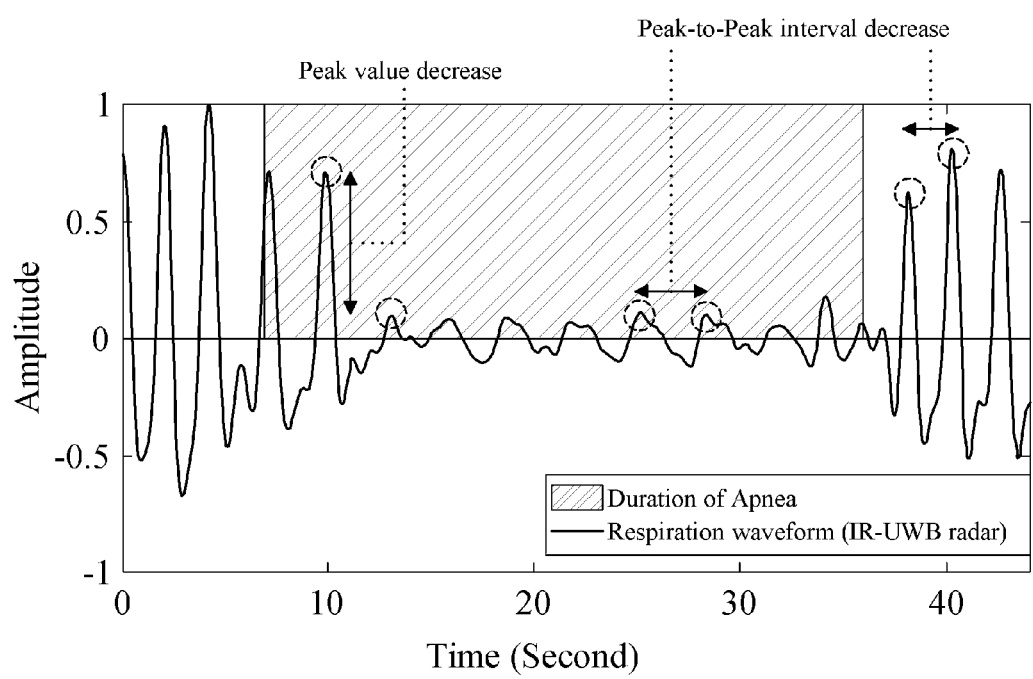
FIG. 5 is a diagram for describing a concept in which the device for detecting and diagnosing sleep apnea according to the present embodiment detects sleep apnea.

FIG. 1 illustrates a schematic structure of a device for detecting and diagnosing sleep apnea according to one embodiment of the present invention, FIG. 2 illustrates an example of an environment for detecting and diagnosing sleep apnea according to the present embodiment, and FIG. 3 illustrates an example of a respiration signal acquired by a respiration waveform extraction unit of FIG. 1. FIGS. 4A-4C illustrate respiratory activities detected at a nose and an abdomen and respiratory signals detected using a radar during central sleep apnea, and FIG. 5 is a diagram for describing a concept in which the device for detecting and diagnosing sleep apnea according to the present embodiment detects sleep apnea.

Referring to FIG. 1, the device for detecting and diagnosing sleep apnea according to the present embodiment includes a signal acquisition unit 10, a respiration signal extraction unit 20, a threshold value setting unit 30, and a detection diagnosis unit 40.

The signal acquisition unit 10 acquires a biosignal for measuring respiration of an examinee in a non-contact/non-invasive manner using an impulse radio ultra-wideband (IR-UWB) radar. The signal acquisition unit 10 includes one or more IR-UWB radars, emits an impulse signal, and acquires a biosignal by removing clutter from a reception signal received when the impulse signal is emitted and reflected.

The IR-UWB radar operates in such a manner that the IR-UWB radar emits a short impulse signal with a width in a unit of several tens of nano/picometers and determines the presence of an object and a distance thereto using a time difference between the impulse signal and a signal received when the short impulse signal is reflected by the object. Since the IR-UWB radar uses a UWB frequency that is harmless to the human body, the IR-UWB radar can detect a subject in a non-contact manner without interference from other sensors. In addition, since the IR-UWB radar has very small transmission power, the IR-UWB radar can be implemented at low power, low price, and small size. Furthermore, by using a ultra wide band, the IR-UWB radar is strong against narrow-band interference, and a spectrum of a signal appears as a pseudo-noise form, and thus, security is also improved.

The signal acquisition unit 10 may include a radar unit 11 and a clutter removal unit 12. The radar unit 11 includes one or more IR-UWB radars and periodically emits impulse signals s(t) having a predetermined waveform to an examinee.

In the present embodiment, as shown in FIG. 2, one or more IR-UWB radars may be disposed to be spaced apart from the examinee by a predetermined distance (for example, 0.5 m in FIG. 2) and may be disposed to face a designated direction so as to facilitate detection of respiration of the examinee. As an example, the IR-UWB radar may be disposed to face a chest or an abdomen at which a change in body due to respiration of the examinee is great.

One or more IR-UWB radars of the radar unit 11 acquire reception signals $r_i(t)$ received when the emitted impulse signals s(t) are reflected by an object. In this case, each of one or more IR-UWB radars may distinguish the reception signals $r_i(t)$ acquired at time intervals between the plurality of impulse signals s(t) periodically emitted, thereby distinguishing the reception signals $r_i(t)$ for the impulse signals s(t). In some cases, when emission time points of the periodically emitted impulse signals s(t) are indistinguishable, an auto-correlation signal for the reception signal $r_i(t)$ is acquired to determine the periodicity of reception signal $r_i(t)$, thereby distinguishing the reception signals $r_i(t)$ for the impulse signals s(t).

The reception signal $r_i(t)$ includes

The impulse signal s(t) is emitted from the radar and delayed and attenuated by being reflected through various paths by a wall, an examinee, and various objects in an indoor environment, and noise n(t) is added thereto. The reflected and noise added signal is received by each of one or more IR-UWB radars. Therefore, the reception signal $r_i(t)$ received by an $i^{th}$ radar may be represented as in Equation 1.

[Equation 1]

$$r_i(t)=\Sigma_{n=1}^{Npath} a_{ni}s(t-\tau_{ni})+n(t)$$

Here, $N_{path}$ denotes the number of paths through which an emitted impulse signal is reflected and received, and $a_{ni}$ and $\tau_{ni}$ respectively denote a scale value and a delay value when the impulse signal is received by the $i^{th}$ radar along an $n^{th}$ path.

When the IR-UWB radar is used, since sleep apnea can be examined only using one radar, descriptions will be provided by assuming here that one IR-UWB radar is used. Therefore, hereinafter, i, which is a radar identifier, will be omitted. However, as described above, the device for detecting and diagnosing sleep apnea according to the present embodiment may include the plurality of IR-UWB radars.

The clutter removal unit 12 may remove clutter from the reception signal $r_i(t)$ in a predetermined manner to acquire a clutter subtraction signal B(t). The impulse signal s(t) emitted from the radar is reflected by various objects other than an examinee, that is, background objects such as a wall, a table, and a chair and is received as the reception signal $r_i(t)$. Therefore, a clutter signal component, which is a component reflected and received by the background object rather than the examinee, should be removed.

In general, since an object corresponding to a background is fixed unlike an examinee, a clutter signal C(t) included in a current reception signal $r_i(t)$ may be acquired using a previously acquired clutter signal C(t−1) as in Equation 2, and the clutter subtraction signal B(t) may be acquired by subtracting the clutter signal C(t) from the reception signal $r_i(t)$ as in Equation 3.

[Equation 2]

$$C(t)+\alpha*C(t-1)+(1-a)*r(t)$$

Here, α is a weight for determining a ratio between the reception signal $r_i(t)$ and the clutter signal C(t) and is a real value in a range of 0<α<1.

[Equation 3]

$$B(t)=r(t)-C(t)$$

The respiration signal extraction unit 20 includes a respiration waveform extraction unit 21 and a peak detection unit 22, extracts a respiration signal V(t) indicating respiration of an examinee from the clutter subtraction signal B(t) acquired by the signal acquisition unit 10, and detects maximum and minimum peak values from the extracted respiration signal V(t).

The respiration waveform extraction unit 21 receives the clutter subtraction signal B(t) from the signal acquisition unit 10. The clutter subtraction signal B(t) appears as a pattern according to a distance d of a path through the impulse signal s(t) signal emitted from the radar is reflected and received. Therefore, when reflection distances are the same at the same distance, the clutter subtraction signals B(t) for the plurality of impulse signals s(t) are acquired as the same pattern, but when a reflection distance is changed, a pattern is changed. When the IR-URB radar emits the impulse signal s(t) toward an examinee, the greatest change occurs at a specific distance due to respiration of the examinee.

Accordingly, the respiration waveform extraction unit 21 obtains a position D(t), at which a change is greatest in a plurality of clutter subtraction signals B(t) acquired during a predetermined signal acquisition period (here, for example, 15 seconds), as in Equation 4.

[Equation 4]

$$D(t)=\text{argmax}(B_d(t-p)-B_d(t))$$

Here, $B_d(t)$ denotes a clutter subtraction signal acquired when a distance to a reflective target object is d in the clutter subtraction signal B(t) at a time t, and p denotes a signal acquisition period.

A respiration signal V(t) having a waveform according to respiration of an examinee may be acquired as in Equation 5 from Equation 4.

[Equation 5]

$$v(t)=B_{D(t)}(t)$$

That is, the respiration signal V(t) is acquired by extracting a clutter subtraction signal $B_{D(t)}(t)$ at a position D(t) at which a change is greatest in the clutter subtraction signal B(t). The peak detection unit 22 detects each of a local maximum value $L_{max}(n)$ and a local minimum value $L_{min}(n)$ for the respiration signal V(t) acquired by the respiration waveform extraction unit 21 according to Equations 6 and 7.

[Equation 6]

$$L_{max}(n)=V(t) \text{ which satisfy } V(t-1/FPS)<V(t) \& V(t)>V(t+1/FPS)$$

[Equation 7]

$$L_{min}(n)=V(t) \text{ which satisfy } V(t-1/FPS)>V(t) \& V(t)<V(t+1/FPS)$$

According to Equation 6, the peak detection unit 22 detects a respiration signal V(t), which is greater than a respiration signal V(t−1/FPS) acquired in previous one frame before the respiration signal V(t) and is greater than a respiration signal V(t+1/FPS) in subsequent one frame after the respiration signal V(t) and obtains the detected respiration signal V(t) as an $n^{th}$ local maximum value $L_{max}(n)$. Here, the FPS is the number of frames per second. That is, when the respiration signal V(t) is greater than the previously acquired respiration signal V(t−1/FPS) and the subsequently acquired respiration signal V(t+1/FPS), the respiration signal V(t) is detected as the local maximum value $L_{max}(n)$.

According to Equation 7, the peak detection unit 22 detects a respiration signal V(t), which is less than a respiration signal V(t−1/FPS) acquired in previous one frame before the respiration signal V(t) and is less than a respiration signal V(t+1/FPS) in subsequent one frame after the respiration signal V(t) and obtains the detected respiration signal V(t) as an $n^{th}$ local minimum value $L_{min}(n)$. That is, when the respiration signal V(t) is less than the previously acquired respiration signal V(t−1/FPS) and the subsequently acquired respiration signal V(t+1/FPS), the respiration signal V(t) is detected as the local minimum value $L_{min}(n)$.

Here, the reason why the peak detection unit 22 compares the respiration signal V(t) with the previously acquired respiration signal V(t−1/FPS) and the subsequently acquired respiration signal V(t+1/FPS) at FPS is to prevent misdetection of the local maximum value $L_{max}(n)$ and the local minimum value $L_{min}(n)$ by setting a guard interval corresponding to a predetermined time (here, for example, one second) at both sides when the local maximum value $L_{max}(n)$ and the local minimum value $L_{min}(n)$ are detected.

As shown in FIG. 3, the respiration signal V(t) does not appear as a sinusoidal waveform, and a very large number of peaks frequently appear near a top and a bottom thereof. Therefore, in the present embodiment, by setting a guard interval, the peak detection unit 22 may detect frames greater and less than a previous frame and a subsequent frame within the guard interval as a maximum value and a minimum value, thereby easily detecting one local maximum value $L_{max}(n)$ and one local minimum value $L_{min}(n)$ within each period.

When the respiration signal extraction unit 20 detects the local maximum and minimum values $L_{max}(n)$ and $L_{min}(n)$ for the respiration signal V(t), the threshold value setting unit 30 sets a threshold value for detecting sleep apnea.

As shown in FIGS. 4A-4C, during apnea, a waveform of a respiration signal V(t) appears as a waveform different from that during eupnea. During central sleep apnea, FIG. 4A illustrates a respiratory activity checked in a nose, FIG. 4B illustrates a respiratory activity checked in an abdomen, and FIG. 4C illustrates the respiration signal V(t) detected using the IR-UWB radar.

Referring to FIGS. 4A-4C, during sleep apnea, a deviation between the local maximum $L_{max}(n)$ and the local minimum value $L_{max}(n)$ for the respiration signal V(t) is greatly changed from that during eupnea. In general, when sleep apnea occurs, the deviation between the local maximum $L_{max}(n)$ and the local minimum value $L_{min}(n)$ becomes very small.

Therefore, sleep apnea may be determined by analyzing the local maximum $L_{max}(n)$ and the local minimum value $L_{min}(n)$ for the respiration signal V(t) acquired by the respiration signal extraction unit 20. However, a waveform of the respiration signal V(t) during eupnea and sleep apnea varies according to an examinee. Therefore, first, it is necessary to generate a threshold value at which a eupnea state and an apnea state of an examinee are distinguishable.

Referring to FIG. 1, the threshold value setting unit 30 may include a first threshold value setting unit 31, a weight setting unit 32, and a second threshold value setting unit 33.

First, the first threshold value setting unit 31 obtains an accumulated deviation between the local maximum value $L_{max}(n)$ and the local minimum value $L_{min}(n)$ for the respiration signal V(t) detected by the respiration signal extraction unit 20 to set a first threshold value Thr1(t) that is a reference value for an eupnea state.

The first threshold value setting unit 31 obtains deviations $(A(n)=L_{max}(n)-L_{min}(n))$ between the local maximum value $L_{max}(n)$ and the local minimum value $L_{min}(n)$ for the respiration signal V(t) for a predetermined time (for example, two minutes before and after t). A deviation corresponding to a predetermined lower proportion among obtained k deviations A(1), A(2), . . . , and A(k) may be set as the first threshold value Thr1(t). As an example, a deviation corresponding to a lower proportion of 30% among the k deviations A(1), A(2), . . . , and A(k) may be set as the first threshold value Thr1(t).

Here, a reason for the first threshold value setting unit 31 to set the first threshold value Thr1(t) by accumulating the deviations A(n) for a predetermined time is because, even when the respiration signal V(t) for the same examinee is acquired, a respiration state of the examinee may be changed over time.

The weight setting unit 32 sets a weight for easily determining an apnea state. Referring to FIG. 5, a peak magnitude is abruptly decreased when apnea occurs. In addition, when apnea is ended, a peak-to-peak interval of the respiration signal V(t) is decreased. That is, the number of peaks of the respiration signal V(t) is increased as compared with that during apnea.

Accordingly, the weight setting unit 32 sets first and second weights weight1($\tau$) and weight2($\tau$) to determine the start and end of an apnea state. Here, first and second weights weight1($\tau_1$) and weight2($\tau_2$) are weights applied during predetermined first and second weight periods $\tau_1$ and $\tau_2$. Here, the first weight period $\tau_1$ may be set, for example, as a period of 30 seconds after a reference time point t (t<$\tau_1$<t+30 seconds), and the second weight period $\tau_2$ may be set, for example, as a period of 30 seconds before the reference time point t (t−30<$\tau$2<t).

When a ratio $(|L_{max}(n-1)/L_{max}(n)|)$ of a previous local maximum value $L_{max}(n-1)$ to a local maximum value $L_{max}(n)$ exceeds a first reference ratio $w_1$, (here, for example, 1.6) $(|L_{max}(n-1)/L_{max}(n)|>w_1)$, that is, when a peak magnitude is abruptly decreased, the weight setting unit 32 sets the first weight weight1($\tau_1$) during the first weight period $\tau_1$ to a first value (here, for example, 1.6) (weight1($\tau_1$)=1.6).

However, when the ratio (|L max(n−1)/L max(n)|) of the previous local maximum value $L_{max}(n-1)$ to the local maximum value $L_{max}(n)$ does not exceed the first reference ratio $w_1$ $(|L_{max}(n-1)/L_{max}(n)|\leq w_1)$, the weight setting unit 32 sets the first weight weight1($\tau_1$) to a second value (here, for example, 1) (weight1($\tau_1$)=1).

As an example, it has been described that the weight setting unit 32 sets the first weight weight1($\tau_1$) based on a change in the local maximum value $L_{max}(n)$, but the weight setting unit 32 may also set the first weight weight1($\tau_1$) based on a change ($|L_{min}(n)/L_{min}(n-1)|$) in the local minimum value $L_{min}(n)$.

In addition, when a ratio (N(t)/N(t+m)) of the number N(t) of peaks (number of the local maximum values $L_{max}(n)$ and the local minimum values $L_{min}(n)$) obtained during a predetermined reference time period m (here, for example, 30 seconds) before the reference time point t and the number N(t+m) of peaks obtained during a reference time period m after the reference time point t is less than a second reference ratio $w_2$ (here, for example, 1.8) (N(t)/N(t+m)<$w_2$), that is, when a peak magnitude is not abruptly increased, the weight setting unit 32 sets the second weight weight2($\tau_2$) during the second weight period $\tau_2$ to a first value (here, for example, 1.8)(weight2($\tau_2$)=1.8).

However, when the ratio (N(t)/N(t+m)) between the numbers of the peaks is greater than or equal to the second reference ratio $w_2$ (N(t)/N(t+m)>$w_2$), the weight setting unit 32 sets the second weight weight2($\tau_2$) to a second value (here, for example, 1)(weight2($\tau_2$)=1).

The second threshold value setting unit 33 sets a second threshold value Thr2(t), which is for detecting an apnea state, according to Equation 8 from the first threshold value Thr1(t) obtained by the first threshold value setting unit 31 and the first and second weights weight1($\tau$) and weight2($\tau$) set by the weight setting unit 32.

[Equation 8]

$$Thr2(t) = weight1(t) * weight2(t) * Thr1(t)$$

The detection diagnosis unit 40 compares the deviation A(n) obtained by the threshold value setting unit 30 with the set second threshold value Thr2(t) to determine an apnea state, and when the apnea state is determined, the detection diagnosis unit 40 diagnoses a level of sleep apnea.

The detection diagnosis unit 40 may include an apnea detection unit 41 and an apnea diagnosis unit 42.

The apnea detection unit 41 determines whether a deviation $A_{65}(n)$ is greater than or equal to the second threshold value Thr2(t) ($A_\gamma(n) \geq Thr2(t)$ in a unit of a predetermined detection period $\gamma$, and when the deviation $A_\gamma(n)$ is greater than or equal to the second threshold value Thr2(t), the apnea detection unit 41 determines the detection period $\gamma$ as an apnea period. Here, as an example, the detection period $\gamma$ may be set to 10 seconds, which is an existing minimum determination time for determining sleep apnea syndromes.

The apnea diagnosis unit 42 diagnoses a level of sleep apnea according to the number c of times of occurrences of an apnea state detected by the apnea detection unit 41 during a sleep time of an examinee.

In the present embodiment, the apnea diagnosis unit 42 may diagnose a level of sleep apnea according to, for example, an apnea hypopnea index (AHI), which is generally used as a severity index of sleep apnea, and the AHI is obtained as the number c of occurrences of the apnea state per total sleep time of an examinee as in Equation 9.

[Equation 9]

$$AHI = \frac{C}{\text{Total sleep time}}$$

A level of sleep apnea is diagnosed according to the obtained AHI in the same manner as in an existing sleep apnea diagnosis method. According to the AHI, when the AHI is less than 5 (AHI<5), sleep apnea is diagnosed as a normal state, when the AHI is greater than or equal to 5 and less than 15 (5≤AHI<15), sleep apnea is diagnosed as mild sleep apnea, when the AHI is greater than or equal to 15 and less than 30 (15≤AHI<30), sleep apnea is diagnosed as moderate sleep apnea, and when the AHI is greater than or equal to 30 (30≤AHI), sleep apnea is diagnosed as severe sleep apnea.

Figure 6:
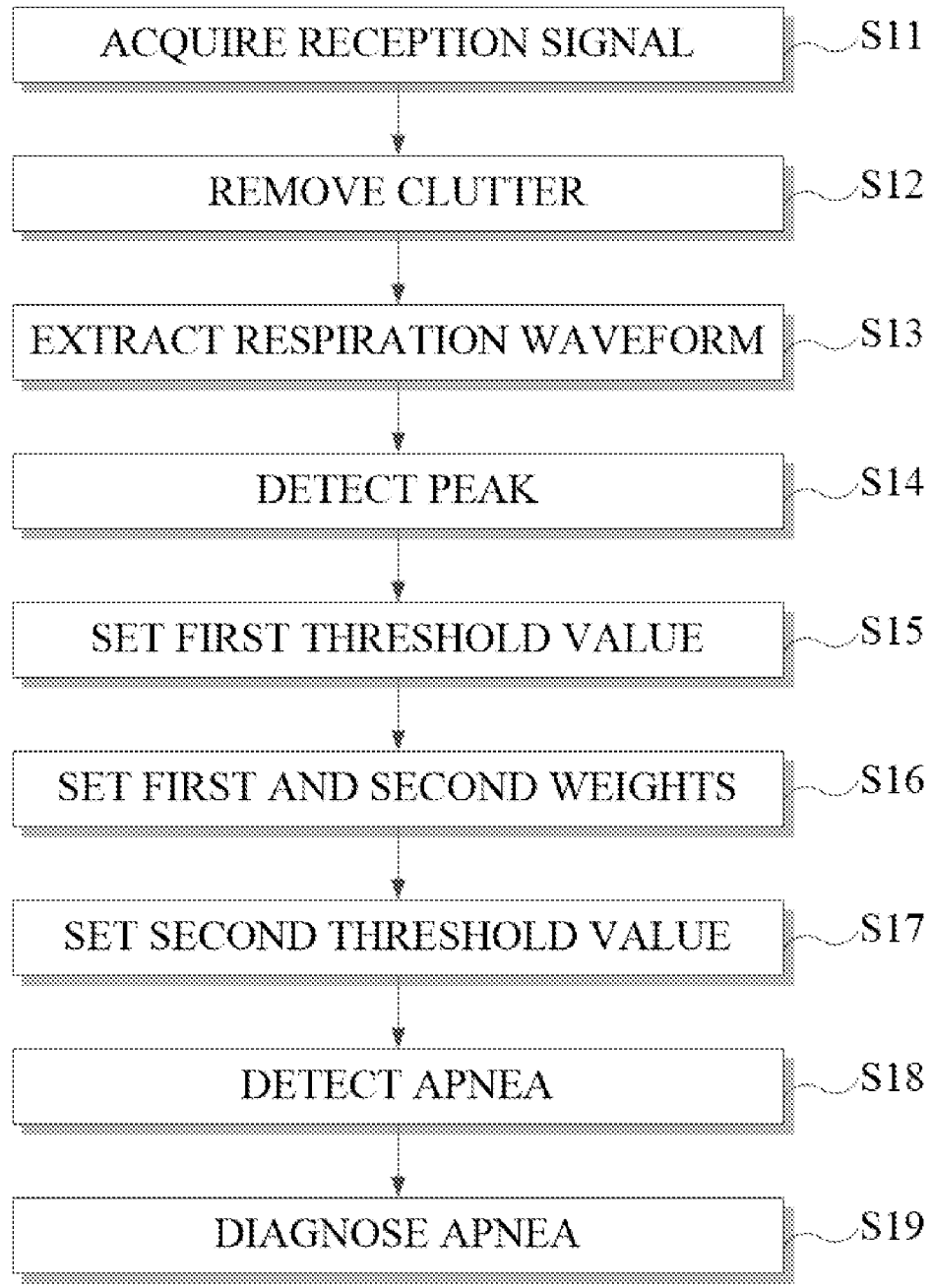
FIG. 6 illustrates a method of detecting and diagnosing sleep apnea according to one embodiment of the present invention.

FIG. 6 illustrates a method of detecting and diagnosing sleep apnea according to one embodiment of the present invention.

Referring to FIGS. 1 to 5, describing the method of detecting and diagnosing sleep apnea of FIG. 6, first, an impulse signal s(t) having a predetermined waveform is periodically emitted to an examinee using one or more IR-URB radars, and a reception signal $r_i(t)$ for the emitted impulse signal s(t) is acquired (S11). A clutter signal C(t) is removed from the reception signal $r_i(t)$ to acquire a clutter subtraction signal B(t)(S12).

When the clutter subtraction signal B(t) is acquired, a position D, at which a change is greatest in a plurality of clutter subtraction signals B(t) acquired during a predetermined signal acquisition period (here, for example, 15 seconds), is determined, and a clutter subtraction signal $B_{D(t)}(t)$ at the determined position D(t) is extracted to acquire a respiration waveform signal V(t)(S13).

When the respiration waveform signal V(t) is acquired, peaks of the acquired respiration waveform signal V(t) are analyzed to detect each of a local maximum value $L_{max}(n)$ and a local minimum value $L_{min}(n)$(S14).

A first threshold value Thr1(t), which is a criterion for an eupnea state of the examinee, is set (S15). A plurality of deviations A(n) between the local maximum value $L_{max}(n)$ and the local minimum value $L_{min}(n)$, which are detected for a predetermined time, are obtained, and the first threshold value Thr1(t) is set to a deviation corresponding to a predetermined lower proportion among the obtained plurality of deviations A(n).

In addition, first and second weights weight1($\tau$) and weight2($\tau$) for determining the start and end of an apnea state are set (S16).

A first weight weight1($\tau_1$) is set to be variable according to a ratio ($|L_{max}(n-1)/L_{max}(n)|$) of a previous local maximum value $L_{max}(n-1)$ to the local maximum value $L_{max}(n)$. When the ratio ($|L_{max}(n-1)/L_{max}(n)|$) of the local maximum value $L_{max}(n)$ to the previous local maximum value $L_{max}(n-1)$ exceeds a first reference ratio $w_1$ ($|L_{max}(n-1)/L_{max}(n)|>w_1$), the first weight weight1($\tau_1$) is set to a predetermined first value, but when the ratio ($|L_{max(n-1)}/L_{max}(n)|$) of the local maximum value $L_{max}(n)$ to the previous local maximum value $L_{max}(n-1)$ does not exceed the first reference ratio $w_1$, the first weight weight1($\tau_1$) is set to a predetermined second value.

In addition, the second weight weight2($\tau_2$) may be set to be variable according to a ratio (N(t)/N(t+m)) of the number N(t) of peaks obtained for a predetermined reference time m before a reference time t to the number N(t+m) of peaks obtained for a reference time m after the reference time point t. When the ratio (N(t)/N(t+m)) between the numbers of the peaks is less than a second reference ratio $w_2$ (N(t)/N(t+m)<$w_2$), the second weight weight2($\tau_2$) during a predetermined second weight period $\tau_2$ is set to a first value, but when the ratio (N(t)/N(t+m)) between the numbers of the peaks is greater than or equal to the second reference ratio $w_2$, the second weight weight2($\tau_2$) during the second weight period $\tau_2$ is set to a second value. A second threshold value Thr2($\tau$) is set from the first threshold value Thr1(t) and the first and second weights weight1($\tau$) and weight2($\tau$)(S17).

When the second threshold value Thr2(t) is set, whether a deviation $A_\gamma(n)$ is greater than or equal to the second threshold value Thr2(t) ($A_\gamma(n) \geq$ Thr2(t)) in a unit of a predetermined detection period γ is determined, and when the deviation $A_\gamma(n)$ is greater than or equal to the second threshold value Thr2(t), the detection period γ is detected as an apnea period (S18).

Thereafter, a level of sleep apnea is diagnosed according to the number c of times of occurrences of the apnea state detected during a total sleep time of the examinee (S19).

The method according to the present invention may be implemented by a computer program stored in a medium so as to execute the method in a computer. Here, a computer readable medium may be any available medium that can be accessed by a computer and may also include all computer storage media. The computer storage media include volatile and nonvolatile media and separable and inseparable media implemented in any method or technology for storage of information such as computer readable instructions, data structures, program modules, or other pieces of data and include a random access memory a read-only memory (ROM), a random access memory (RAM), a compact disk (CD)-ROM, a digital video disk (DVD)-ROM, magnetic tape, a floppy disk, and an optical data storage device.

Although the present invention has been described with reference to the embodiments shown in the drawings, this is merely exemplary, and it should be understood by those skilled in the art that various modifications and other equivalent embodiments are possible from the embodiments.

Accordingly, the true technical protection scope of the present invention should be determined by the technical spirit of the appended claims.

The invention claimed is:

1. A device for detecting and diagnosing sleep apnea, the device comprising:
  a signal acquisition unit configured to acquire clutter subtraction signals by removing a clutter signal from reception signals received when impulse signals are emitted from one or more impulse radio ultra-wideband (IR-UWB) radars disposed at predetermined positions and are reflected;
  a respiration signal extraction unit configured to determine a position at which a change is greatest in the plurality of clutter subtraction signals acquired during a predetermined signal acquisition period, extract the clutter subtraction signal at the determined position to acquire a respiration signal that is a respiration waveform signal, and detect a local maximum value and a local minimum value that are peaks of the respiration signal;
  a threshold value setting unit configured to accumulate deviations between the local maximum value and the local minimum value to set a first threshold value that is a criterion for a normal state, set a first weight for determining a start of an apnea state according to a change in the local maximum value or the local minimum value, set a second weight for determining an end of the apnea state according to a change in the number of the local maximum values and the local minimum values obtained during a predetermined reference time period, and set a second threshold value, which is a criterion for determining the apnea state, from the first threshold value and the first and second weights; and
  a detection diagnosis unit configured to compare the deviation with the second threshold value to detect the apnea state and diagnose a level of sleep apnea of an examinee based on the number of times of the detected apnea state.

2. The device of claim 1, wherein the threshold value setting unit includes:
  a first threshold value setting unit configured to accumulate the deviations between the local maximum value and the local minimum value and set a deviation corresponding to a predetermined lower proportion among the accumulated deviations as the first threshold value;
  a weight setting unit configured to compare a ratio of a previous local maximum value to a current local maximum value or a ratio of a previous local minimum value to the local minimum value with a predetermined first reference ratio at a reference time point, set the first weight to different predetermined values according to a comparison result, and set the second weight to different predetermined values according to a ratio of the number of the local maximum values and the local minimum values obtained during the reference time period before the reference time point to the number of the local maximum values and the local minimum values obtained during the reference time period after the reference time point; and
  a second threshold value setting unit configured to set the second threshold value by multiplying the first threshold value changed over time by the first and second weights.

3. The device of claim 2, wherein the weight setting unit applies the first weight during a predetermined first weight period from the reference time point and applies the second weight during a predetermined second weight period before the reference time point.

4. The device of claim 3, wherein the weight setting unit includes:
  an apnea detection unit configured to compare the deviation with the second threshold value in a unit of a predetermined detection period and, when the deviation is greater than or equal to the second threshold value, detect the apnea state; and
  an apnea diagnosis unit configured to determine the level of sleep apnea of the examinee according to the number of times of the detected apnea state per total sleep time.

5. A method of detecting and diagnosing sleep apnea, the method comprising:
  removing a clutter signal from reception signals, which are received when impulse signals are emitted from one or more impulse radio ultra-wideband (IR-UWB) radars disposed at predetermined positions and are reflected, to acquire clutter subtraction signals;
  determining a position at which a change is greatest in the plurality of clutter subtraction signals acquired during a predetermined signal acquisition period, extracting the clutter subtraction signal at the determined position to acquire a respiration signal that is a respiration waveform signal, and detecting a local maximum value and a local minimum value that are peaks of the respiration signal;
  accumulating deviations between the local maximum value and the local minimum value to set a first threshold value that is a criterion for a normal state, setting a first weight for determining a start of an apnea state according to a change in the local maximum value or the local minimum value, setting a second weight for determining an end of the apnea state according to a change in the number of the local maximum values and the local minimum values obtained during a predetermined reference time period, and setting a second threshold value, which is a criterion for determining the apnea state, from the first threshold value and the first and second weights; and comparing the deviation with the second threshold value to detect the apnea state and diagnosing a level of sleep apnea of an examinee based on the number of times of the detected apnea state.

6. The method of claim 5, wherein the setting of the second threshold value includes:

accumulating the deviations between the local maximum value and the local minimum value and setting a deviation corresponding to a predetermined lower proportion among the accumulated deviations as the first threshold value;

comparing a ratio of a previous local maximum value to a current local maximum value or a ratio of a previous local minimum value to the local minimum value with a predetermined first reference ratio at a reference time point, and setting the first weight to different predetermined values according to a comparison result;

setting the second weight to different predetermined values according to a ratio of the number of the local maximum values and the local minimum values obtained during the reference time period before the reference time point and the number of the local maximum values and the local minimum values obtained during the reference time period after the reference time point; and multiplying the first threshold value changed over time by the first and second weights to set the second threshold value.

7. The method of claim 6, wherein the setting of the first weight includes applying the first weight during a predetermined first weight period from the reference time point; and the setting of the second weight includes applying the second weight during a predetermined second weight period before the reference time point.

8. The method of claim 7, wherein the diagnosing of the level of sleep apnea includes:

comparing the deviation with the second threshold value in a unit of a predetermined detection period and, when the deviation is greater than or equal to the second threshold value, detecting the apnea state; and determining the level of sleep apnea of the examinee according to the number of times of the detected apnea state per total sleep time.

* * * * *